United States Patent [19]
Cimarusti et al.

[11] 3,971,773
[45] July 27, 1976

[54] STEROIDAL 9,11 β-DIHALO-[16α,17-b]1,4-DIOXANES

[75] Inventors: Christopher M. Cimarusti, Hamilton; Frank L. Weisenborn, Titusville; Seymour D. Levine, North Brunswick, all of N.J.

[73] Assignee: E. R. Squibb & Sons, Inc., Princeton, N.J.

[22] Filed: June 2, 1975

[21] Appl. No.: 583,149

Related U.S. Application Data

[63] Continuation-in-part of Ser. No. 522,195, Nov. 8, 1974, abandoned.

[52] U.S. Cl. .................. 260/239.55 R; 260/239.57; 260/397.45
[51] Int. Cl.$^2$ ........................................ C07D 471/00
[58] Field of Search ................. 260/239.55, 239.57, 260/239.55 R

*Primary Examiner*—Elbert L. Roberts
*Attorney, Agent, or Firm*—Lawrence S. Levinson; Merle J. Smith; Donald J. Barrack

[57] ABSTRACT

A series of novel steroidal 9,11β-dihalo-[16α,17-b]-1,4-dioxanes is disclosed herein. These compounds are useful as anti-inflammatory agents.

10 Claims, No Drawings

STEROIDAL 9,11β-DIHALO-[16α,17-b]1,4-DIOXANES

This is a continuation-in-part of copending U.S. patent application Ser. No. 522,195, filed Nov. 8, 1974 now abandoned.

SUMMARY OF THE INVENTION

Steroids having the formula

I
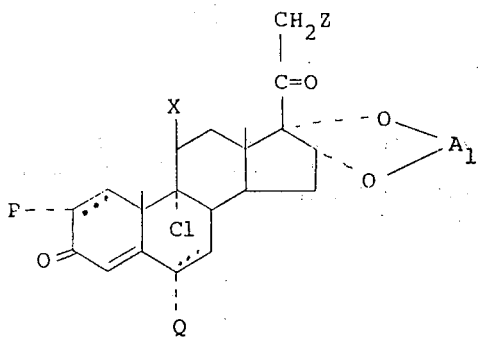

are useful as anti-inflammatory agents. In formula I, and throughout the specification, the symbols are as defined below:

Z can be hydrogen, hydroxyl, acyloxy of the formula

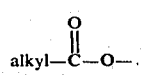

or

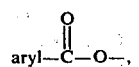

or halogen;
X can be chlorine or fluorine;
$A_1$ can be —$CH_2$—$CH_2$—,

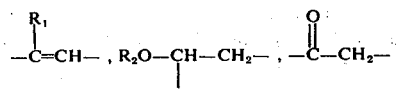

or

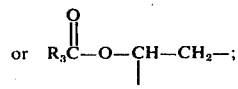

P and Q are independent of each other and each can be hydrogen, methyl, or halogen;
$R_1$ can be hydrogen, alkyl or aryl;
$R_2$ can be hydrogen or alkyl; and
$R_3$ can be alkyl, cycloalkyl, or aryl.

The dotted lines in the 1, 2 and 6, 7 -positions of the steroids of this invention, represent the optional presence of double bonds.

The term "alkyl", as used throughout the specification, refers to both branched and straight chain alkyl groups having 1 to 8 carbon atoms. Alkyl groups of 1 to 4 carbon atoms are preferred.

The term "cycloalkyl", as used throughout the specification, refers to cycloalkyl groups having 3 to 6 carbon atoms.

The term "aryl", as used throughout the specification, refers to phenyl or phenyl substituted with halogen, alkyl, or alkyl-O-. Phenyl is the preferred aryl group.

The term "halogen", as used throughout the specification, refers to fluorine, chlorine, bromine, and iodine.

DETAILED DESCRIPTION OF THE INVENTION

The steroids of formula I are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a dosage range of 0.1 to 200 milligrams, preferably 0.3 to 100 milligrams. If administered topically, the compounds of this invention may be used in the range of 0.01 to 5.0% by weight, preferably 0.05 to 2.0% by weight, in a conventional cream or lotion.

Those steroids of formula I wherein $A_1$ is —$CH_2$—$CH_2$—,

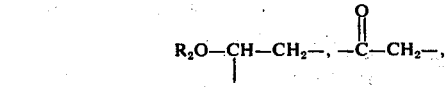

or

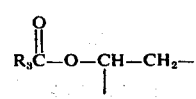

(this subgrouping is referred to hereinafter as $A_2$) are prepared from the corresponding 11β-hydroxy steroid of the structure II
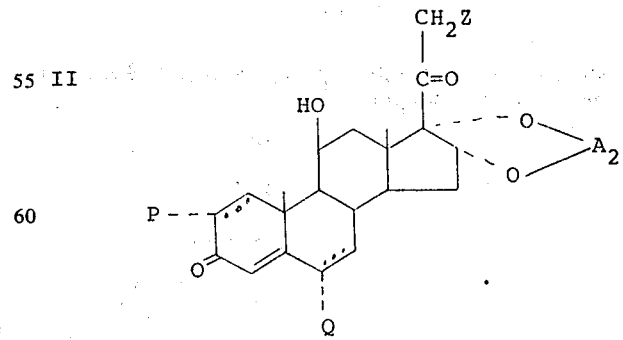

The dehydration of 11β-hydroxy steroids of formula II to yield $\Delta^{9(11)}$-steroids having the structure

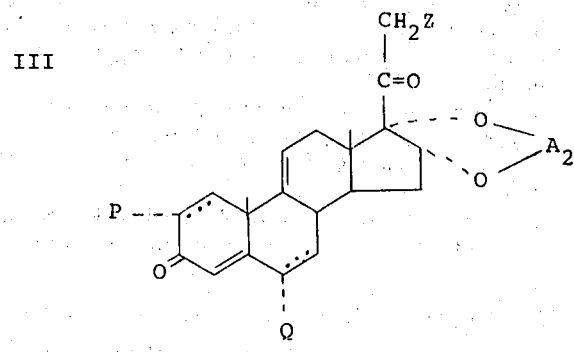

can be carried out using any one of several processes known in the art. Exemplary of such processes are:
1. dehydration with phosphorous oxychloride and pyridine; and
2. dehydration with methanesulfonyl chloride and pyridine.

Reaction of a $\Delta^{9(11)}$-steroid of formula III with N-chlorosuccinimide and an acid of the formula

     IV yields the corresponding steroidal 9,11β-dihalo-[16α,17-b]-1,4-dioxane having the structure

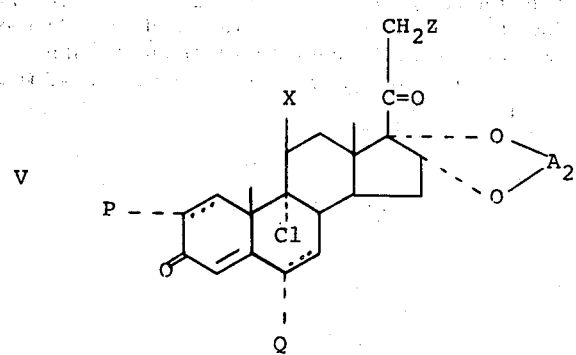

The reaction can be run in a solvent, e.g., glacial acetic acid at a temperature of from 0°C to 30°C, for 1 hour to 6 hours.

Those steroids of formula I wherein $A_1$ is

are prepared from the corresponding 11β-hydroxy steroids of the structure

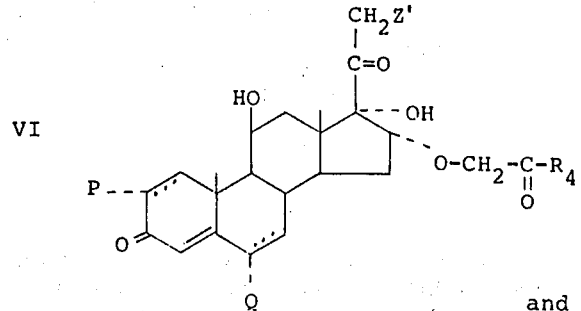

and

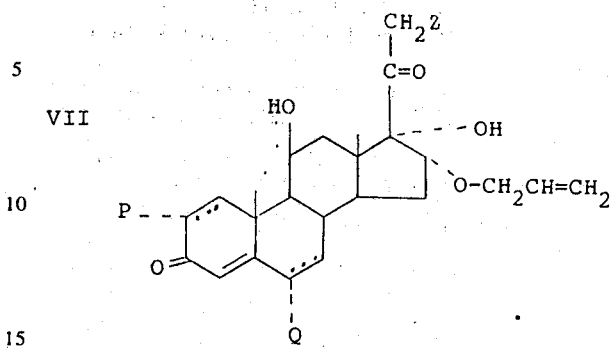

In formulas VI and VII, and throughout the specification, $R_4$ is alkyl or aryl, and Z' is hydrogen, acyloxy of the formula alkyl

or aryl

or halogen.

Conversion of an 11β-hydroxy steroid of formula VI to the corresponding 9,11β-dihalo steroid can be accomplished using the procedures described above (i.e., dehydration of the 11β-hydroxy steroid followed by halogenation). The resultant 9,11β-dihalo steroid can be reacted with a slurry or solution of an organic acid such as p-toluenesulfonic acid, in an organic solvent such as benzene, to yield the corresponding steroid of structure VIII wherein $R_1$ is alkyl or aryl. Conversion of an 11β-hydroxy steroid of formula VII to the corresponding 9,11β-dihalo steroid can be accomplished using the procedures described above (i.e., dehydration of the 11β-hydroxy steroid followed by halogenation). The resultant 9,11β-dihalo steroid can be reacted successively with a peracid, an oxidizing agent, and a slurry of an acid in a solvent such as benzene, to yield a steroid having the structure

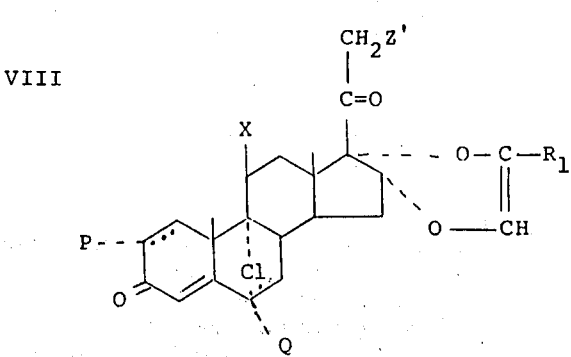

wherein $R_1$ is hydrogen. The corresponding 21-hydroxy steroids are prepared by saponification of a 21-acyloxy steroid.

Cycloborate esters of 16α,17-dihydroxy steroids having the formula

IX
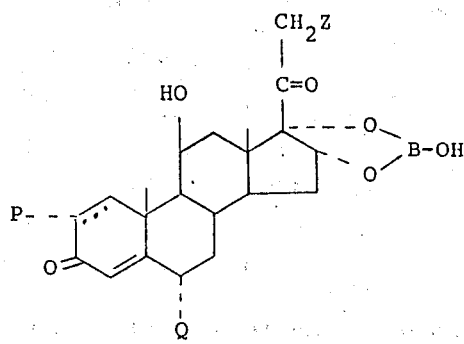

can be used for the preparation of the steroids of formulas II, VI and VII. The cycloborate esters of formula IX are known; see; for example, U.S. Pat. No. 2,831,003, issued Apr. 15, 1958.

Diazoalkenes having the formula

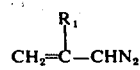   X are also used for the preparation of the steroids of formula II wherein $A_2$ is

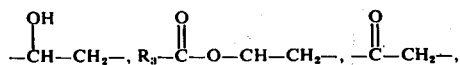

or $-CH_2-CH_2-$ and the steroids of formula VI and VII. In formula X, those diazoalkenes wherein $R_1$ is hydrogen or alkyl are known; see, for example, the *Journal of the American Chemical Society*, 91, 711 (1969). The preparation of the diazoalkene of formula X wherein $R_1$ is aryl is described in the examples of this specification.

Reaction of a cycloborate ester of formula IX with a diazoalkene of formula X yields a steroid having the formula XI
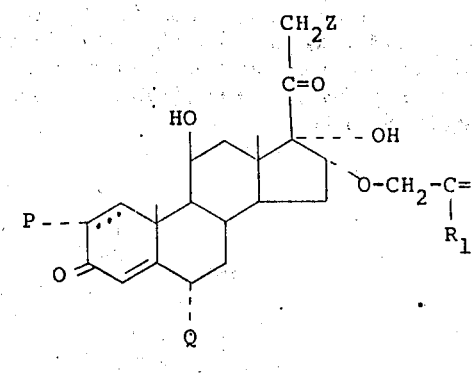

The reaction can be conducted in an organic solvent, preferably a lower alkanol such as methanol, at a temperature of about −10°C to +40°C for about 30 minutes to 4 hours, preferably at 0°C to 20°C for 30 minutes to 1 hour. The steroid and the diazoalkene are reacted in at least a 1:4 molar ratio.

The steroid of formula XI (if Z is hydroxy, it should first be protected by acylation) can be reacted with m-chloroperbenzoic acid to yield a steroid having the formula XII
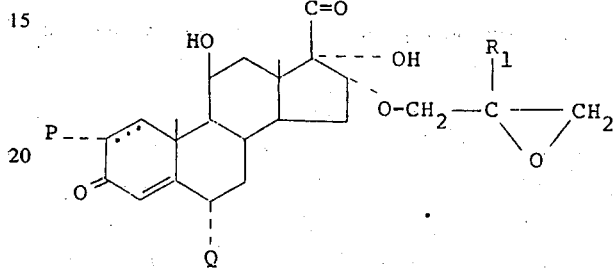

The reaction can be conducted in an organic solvent, preferably a halogenated hydrocarbon such as dichloromethane, at a temperature of from about 0°C to 40°C for about 1 hour to 96 hours, preferably at room temperature for about 2 hours to 72 hours. The steroid of formula XI and the m-chloroperbenzoic acid are reacted in approximately a 1:1 molar ratio.

Reaction of a steroid of formula XII when $R_1$ is alkyl or aryl, with a strong oxidizing agent such as periodic acid, yields a steroid having the formula XIII
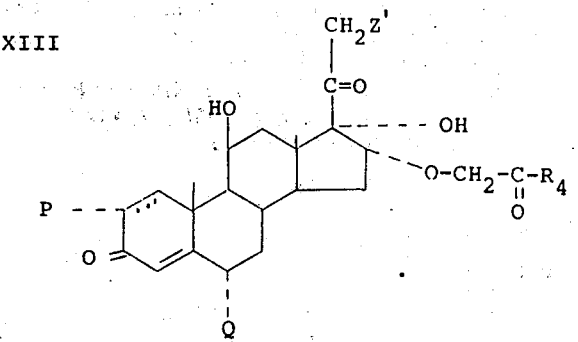

Reaction of a steroid of formula XII when $R_1$ is hydrogen yields a cyclic lactol (formula XIV) which is in equilibrium with the corresponding aldehyde (formula XIVa), i.e.,

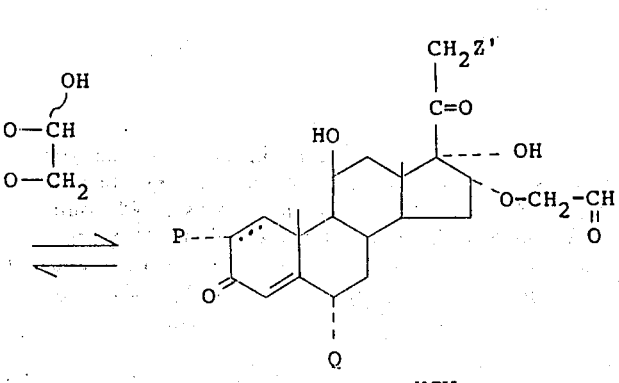

XIV    XIVa

These oxidation reactions can be conducted in an organic solvent, such as tetrahydrofuran, mixed with water at a temperature of about 0°C to 40°C, for about 1 hour to 8 hours, preferably at room temperature for 2 hours to 4 hours.

Reaction of a steroid of formula XIV with an anhydride having the formula

yields a steroidal [16α,17-b]1,4-dioxane having the formula

XV 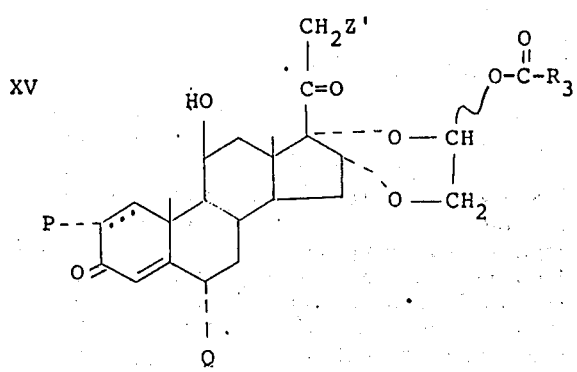

The reaction can be conducted in an organic solvent such as pyridine at a temperature of about 0°C to 40°C for about 30 minutes to 4 hours, preferably at room temperature for 1 hour to 2 hours.

Oxidation of a steroid of formula XIV with Fetizon's reagent (*Angew. Chem. Internat. Edit.*, 8, 444 (1969)) yields a steroid having the formula XVI 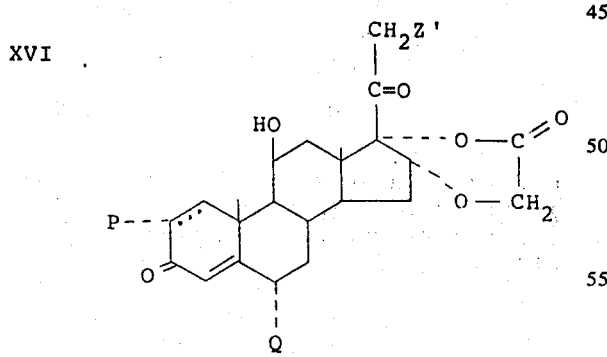

The reaction can be conducted in an organic solvent such as benzene, toluene, etc. at a temperature of about 80°C to 110°C for about 2 hours to 48 hours, preferably at reflux temperature for about 24 hours.

Reaction of a steroid of formula XIV with sodium borohydride yields a steroid having the formula XVII 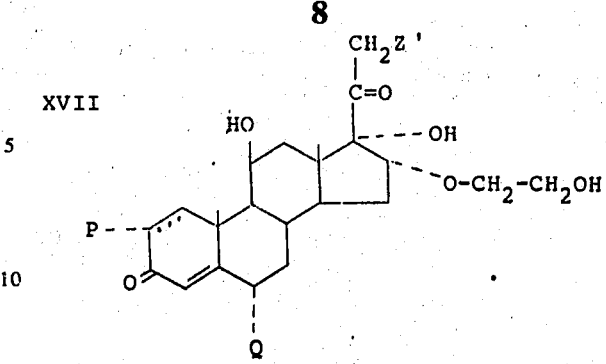

The reaction can be carried out in an organic solvent, preferably a lower alkanol such as methanol at a temperature of from about −10°C to 20°C for about 10 to 60 minutes, preferably at about 20°C for 10 minutes to 30 minutes.

A 16α-hydroxyethoxy steroid of formula XVII can be reacted with a methanesulfonyl halide (methanesulfonyl chloride is preferred) to yield a steroid having the formula XVIII 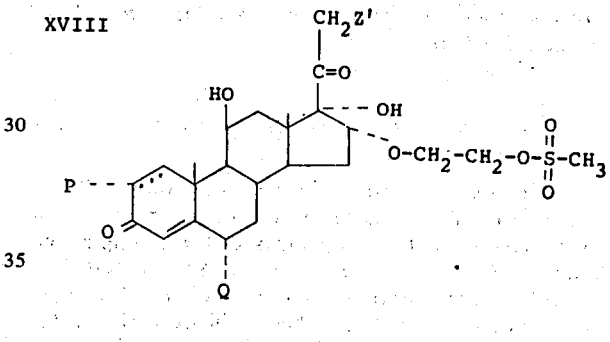

The reaction can be carried out in an organic solvent such as pyridine, in an inert atmosphere, at a temperature of about −10°C to 40°C for 30 minutes to 4 hours, preferably at about 0°C for 1 hour to 2 hours.

Reaction of a steroid of formula XVIII with sodium bicarbonate in a dipolar aprotic solvent such as dimethylsulfoxide yields a steroidal[16α,17-b]1,4-dioxane having the formula XIX 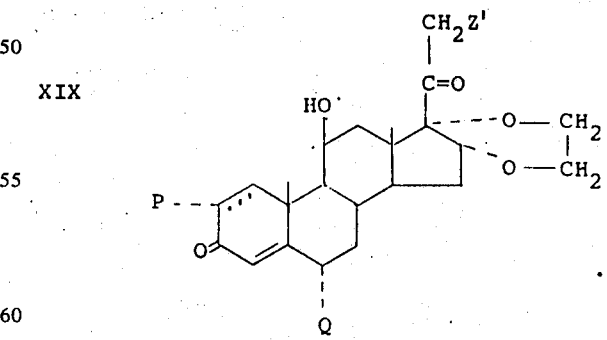

The reaction can be conducted at a temperature of from about 60°C to 130°C for about 1 hour to 24 hours, preferably at about 100°C for 2 hours to 4 hours.

The 21-hydroxy steroid analogs of the steroids of formulas XIV, XIVa, XV, XVI and XIX are readily obtainable by saponification of the corresponding 21-acyloxy steroids.

Steroidal[16α,17-b]1,4-dioxanes of formula II can be prepared from the cycloborate esters of 16α,17-dihydroxy steroids of formula IX and diazoethers having the formula

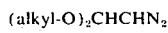

(alkyl-O)₂CHCHN₂    XX

The diazoethers of formula XX are known; see, for example, *Chem. Ber.* 100, 1491 (1967).

Reaction of a cycloborate ester of formula IX with a diazoether of formula XX yields a steroid having the formula

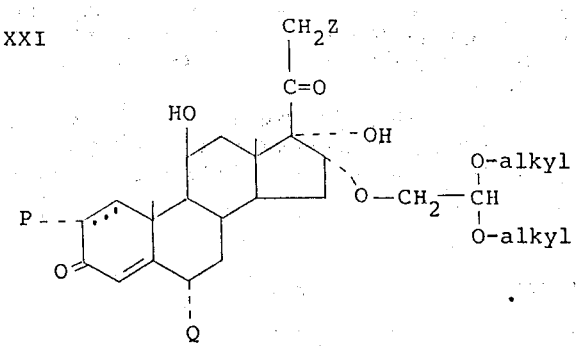

XXI

The reaction can be conducted in an organic solvent, preferably a lower alkanol such as methanol, at a temperature of from about −10°C to 40°C until nitrogen evolution ceases. The preferred reaction temperature is from 0°C to 20°C.

The steroid of formula XXI can be reacted with an organic acid such as p-toluenesulfonic acid in an organic solvent such as benzene to yield a steroidal[-16α,17-b]1,4-dioxane having the formula

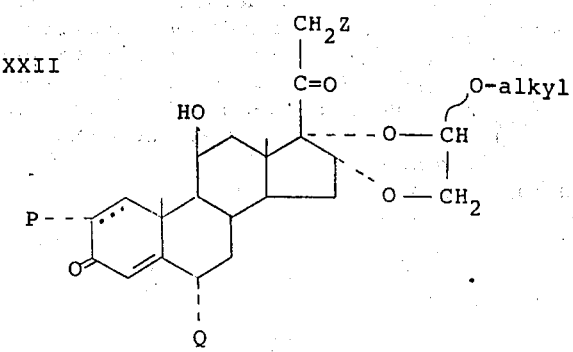

XXII

The reaction can be carried out at a temperature of about 60°C to 140°C for about 1 hour to 24 hours, preferably 80°C to 110°C for 2 hours to 4 hours.

Reaction of a steroid of formula XXI with a mineral acid, e.g., hydrochloric acid, yields a steroidal[16α,17-b]-1,4-dioxane of formula XIV. The reaction can be carried out in an organic solvent such as tetrahydrofuran at a temperature of from about 0°C to 100°C for about 1 hour to 24 hours, preferably 40°C to 60°C for 2 hours to 8 hours.

A steroid of formula XIV can be used to obtain a steroid of formula XV, a steroid of formula XVI and a steroid of formula XIX following the procedures set forth above. The 21-hydroxy analogs are readily obtainable as described above.

Steroidal[16α,17-b]1,4-dioxanes of formula II wherein A₂ is —CH₂—CH₂— can be prepared from the cycloborate esters of 16α,17-dihydroxy steroids of formula IX and 2-(tetrahydropyran-2-yloxy)-1-diazoethane, the preparation of which is set forth in the examples below.

Reaction of a cycloborate ester of formula IX with 2-(tetrahydropyran-2-yloxy)-1-diazoethane yields a steroid having the formula

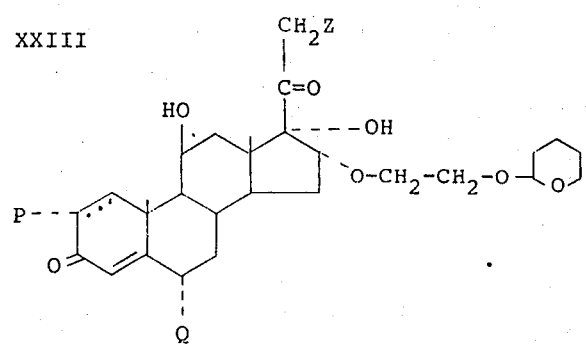

XXIII

The reaction can be carried out in an organic solvent, preferably a lower alkanol such as methanol, at a temperature of from about −10°C to 40°C, preferably 0°C to 20°C. The reaction is continued until nitrogen evolution ceases.

A steroid of formula XXIII (if Z is hydroxy, it should first be protected by acylation) may be cleaved with an acid to yield a steroid of formula XVIII. The cleavage reaction can be conducted in water at a temperature of from about 0°C to 40°C, preferably at room temperature, for about 1 hour to 24 hours, preferably 2 hours to 8 hours. Both organic and inorganic acids can be used in this reaction. The preparation of a steroid of formula II wherein A₂ is —CH₂—CH₂— from a steroid of formula XVII is set forth above.

This invention specifically contemplates the Δ⁴-, Δ¹,⁴-, Δ⁴,⁶-, and Δ¹,⁴,⁶-pregnenes of formula I. The Δ⁴- and Δ¹,⁴-pregnenes are preferred. Those steroids of formula II, VI and VII containing ethylenic unsaturation in the 6,7-position can be prepared as described above with the additional step of selectively introducing a carbon-carbon double bond in the 6,7-position of either a cycloborate ester of a 16α,17-dihydroxy steroid of formula IX or a steroid product of formula XIII, XV, XVI, XIX, or XXII, without effecting other functional groups of the steroid. Exemplary of the oxidizing agents which meet the above requirements is 2,3-dichloro-5,6-dicyano-1,4-benzoquinone when used in the presence of an acid. About one molar equivalent of the oxidizing agent is used per molar equivalent of steroid. The oxidation reaction can be conducted in an organic solvent such as benzene, toluene, dioxane, etc.; dioxane is preferred. The reaction can be carried out for about 1 hour to 96 hours at a temperature of about 50°C to 150°C, preferably for about 4 to 24 hours at about 70°C to 130°C. Alternatively, a Δ⁴,⁶- or Δ¹,⁴,⁶-pregnene corresponding to formula IX may be used as a starting material. These may be prepared by reacting the known Δ⁴,⁶- or Δ¹,⁴,⁶-pregnene-16α,17-diols with boric anhydride as described in U.S. Pat. No. 2,831,003.

Additional methods for the preparation of the compounds of this invention will be readily apparent to a person of ordinary skill in the steroid art. For example, those steroids of this invention having a halogen in the 21-position can be prepared from the corresponding 21-hydroxy steroid by reacting the latter with an alkyl or aryl sulfonyl halide (e.g., methanesulfonyl chloride or p-toluenesulfonyl chloride), in the presence of an organic base such as pyridine, to yield a 21-alkyl (or aryl) sulfonyloxy steroid. The 21-alkyl (or aryl)sulfonyloxy steroid intermediate can be reacted with alkali metal halide (e.g., potassium fluoride, lithium chloride, lithium bromide, sodium iodide, etc.) to yield the corresponding 21-halo steroid.

Using procedures well known to those of ordinary skill in the steroid art it is also possible to prepare 21-acyloxy steroids of this invention from the corresponding 21-hydroxy steroids. Other variations will be apparent to the practitioner of this invention.

The following examples are specific embodiments of this invention.

EXAMPLE 1

9,11β-Dichloro-21-hydroxypregna-1,4-dieno[16α,17-b]-[1,4]dioxane-3,20-dione, 21-acetate A. 16α-[2-(Tetrahydropyran-2-yloxy)ethoxy]-11β,17,21-trihydroxypregna-1,4-diene-3,20-dione a. Tetrahydropyran-2-yloxy acetonitrile This material is prepared by the method of J. Davoll and D. H. Laney, *J. Chem. Soc.*, 2129 (1956) and has a boiling point of 78°-79°C at 2 mm.

b. 2-(Tetrahydropyran-2-yloxy)ethylamine

A solution of 35 g of tetrahydropyran-2-yloxy acetonitrile in 100 ml of ether is added dropwise to a slurry of 10 g of lithium aluminum hydride in 300 ml of ether and 100 ml of tetrahydrofuran. The slurry is refluxed for 210 minutes, cooled, and 25 ml of saturated potassium carbonate solution is added at a rate that maintains gentle reflux. After 90 minutes the slurry is filtered and the solid is washed with ether. The filtrate is evaporated in vacuo and distilled to give 33.6 g of 2-(tetrahydropyran-2-yloxy)-ethylamine, boiling point 41.5° - 46°C at 0.5-0.8 mm.

c. N-[2-(Tetrahydropyran-2-yloxy)ethyl]urea

A mixture of 33.2 g of 2-(tetrahydropyran-2-yloxy)-ethylamine, 50 g of ice, and a solution of 35 g of potassium isocyanate in 80 ml of water is stirred well as 45.6 ml of 5N hydrochloric acid (cooled to −40°C) is added in one portion. The resulting solution is refluxed for 90 minutes, cooled, and extracted with four 150 ml portions of chloroform. The chloroform extract is dried and evaporated in vacuo to give 39.6 g of oil.

d. N-Nitroso-N-[2-(tetrahydropyran-2-yloxy)-ethyl]urea

A solution of 39.6 g of N-[2-(tetrahydropyran-2-yloxy)ethyl]urea in 400 ml of ether and 100 ml of methylene chloride is slurried with 50 g of sodium acetate and cooled to −10°C with mechanical stirring. A solution of 30 g of nitrogen dioxide in 100 ml of ether is added over a 30 minute period, the slurry is stirred at −10°C for 20 minutes and then filtered. The filtrate is washed with saturated sodium bicarbonate solution, dried, and evaporated to give 41.8 g of yellow oil.

e. 2-(Tetrahydropyran-2-yloxy)-1-diazoethane

A solution of 41.8 g of N-nitroso-N-[2-(tetrahydropyran-2-yloxy)ethyl]urea in 200 ml of ether and 100 ml of pentane is added to 450 ml of 1N sodium hydroxide solution at 1°-4°C over a 25 minute period. The solution is stirred for an additional 30 minutes and the layers are separated. The organic layer is dried over sodium hydroxide pellets at 20°C for 5 minutes, and then filtered.

f. 16α-[2-(Tetrahydropyran-2-yloxy)ethoxy]-11β,17,21-trihydroxypregna-1,4-diene-3,20-dione A solution of 2-(tetrahydropyran-2-yloxy)-1-diazoethane (prepared from 69.1 g of N-]2-(tetrahydropyran-2-yloxy)ethyl]urea by the procedure described in (a) – (e) above) in 600 ml of 3:1 ether-pentane is stirred with 200 ml each of ether and methanol at 0°C. Fourteen g of 11β,16α,17,21-tetrahydroxypregna-1,4-diene-3,20-dione, 16,17-cycloborate is added in portions. After nitrogen evolution ceases the solvents are removed in vacuo and the residue is dissolved in chloroform and chromatographed on a 150 g-silica gel column. Elution with chloroform and then 1:1 chloroformethyl acetate gives 4.0 g of TLC pure 16α-[2-(tetrahydropyran-2-yloxy)ethoxy]-11β,17,21-trihydroxypregna-1,4-diene-3,20-dione.

B. 16α-[2-(Tetrahydropyran-2-yloxy)ethoxy]-11β,17,21-trihydroxypregna-1,4-diene-3,20-dione, 21-acetate A solution of 3.75 g of 16α-[2-tetrahydropyran-2-yloxy)ethoxy]-11β,17,21-trihydroxypregna-1,4-diene-3,20-dione in 15 ml of pyridine and 5 ml of acetic anhydride is kept at room temperature for 4 hours and the solvents are then evaporated in vacuo. The residue is dissolved in chloroform and washed with dilute hydrochloric acid, water, dilute sodium bicarbonate solution, and dried. Solvent removal gives 4.9 g of crude 16α-[2-(tetrahydropyran-2-yloxy)ethoxyl]-11β,17,21-trihydroxypregna-1,4-diene-3,20-dione, 21-acetate.

C. 16α-(2-Hydroxyethoxy)-11β,17,21-trihydroxypregna-1,4-diene-3,20-dione, 21-acetate A solution of 4.9 g of crude 16α-[2-(tetrahydropyran-2-yloxy)ethoxy]-11β,17,21-trihydroxypregna-1,4-diene-3,20-dione, 21-acetate in 60 ml each of acetic acid and water is stirred for 6 hours at room temperature. The solvents are removed in vacuo and the residue is dissolved in chloroform and washed with 5% sodium bicarbonate solution and dried. Solvent removal gives 3.9 g of product which is combined with 750 mg of product from a different batch and chromatographed on a 90 g-silica gel column. Elution with chloroform and then 1:1 chloroform-ethyl acetate gives 3.7 g of material which crystallizes from acetone-hexane to give 3.17 g of 16α-(2-hydroxyethoxy)-11β,17,21-trihydroxypregna-1,4-diene-3,20-dione, 21-acetate, melting point 138°-140°C.

D. 16α-(2-Mesyloxyethoxy)-11β,17,21-trihydroxypregna-1,4-diene-3,20-dione, 21-acetate A solution of 3.0 g of 16α-(2-hydroxyethoxy)-11β,17,21-trihydroxypregna-1,4-diene-3,20-dione, 21-acetate in 15 ml of pyridine is stirred with 0.75 ml of methanesulfonyl chloride at 0°C for 150 minutes. The mixture is poured into 1.5 liter of cold 1N hydrochloric acid, stirred for a short time, and filtered. The resulting solid is dissolved in chloroform, washed with water, dried, and evaporated in vacuo to give 4.0 g of crude 16α-(2-mesyloxyethoxy)-11β,17,21-trihydroxypregna-1,4-diene-3,20-dione, 21-acetate.

E. 11β,21-Dihydroxypregna-1,4-dieno[16α,17-b]-[1,4]dioxane-3,20-dione, 21-acetate A solution of 4.0 g of crude 16α-(2-mesyloxyethoxy)-11β,17,21-trihydroxypregna-1,4-diene-3,20-dione, 21-acetate in 200 ml of dimethylsulfoxide is stirred at 110°C under nitrogen, with 4.0 g of sodium bicarbonate for 2 hours. The slurry is cooled, poured into 2 liters of cold 2.5% hydrochloric acid, and extracted with chloroform (three 250 ml portions). The chloroform solution is washed with two 1 liter portions of 2.5% hydrochloric acid, dried, and evaporated in vacuo. The residue is dissolved in chloroform and chromatographed on a 66 g-silica gel column. Elution with chloroform gives 2.4 g of material which crystallizes from acetone-hexane to give 1.55 g of 11β,21-dihydroxypregna-1,4-dieno[16α,17-b][1,4]dioxane-3,20-dione, 21-acetate, melting point 280°–282°C.

F. 21-Hydroxypregna-1,4,9(11)-trieno[16α,17-b]-[1,4]dioxane-3,20-dione, 21-acetate A mixture of 1.5 g of 11β,21-dihydroxypregna-1,4-dieno[16α,17-b][1,4]dioxane-3,20-dione, 21-acetate, 75 ml of dimethylformamide, 37.5 ml of pyridine, and 15 ml of methanesulfonyl chloride is stirred at 0°C for 75 minutes, poured into cold dilute hydrochloric acid, and the resulting mixture extracted with chloroform. The chloroform solution is dried and evaporated in vacuo. The residue is dissolved in chloroform and chromatographed on a 60 g-silica gel column. Elution with 1:1 hexane-chloroform gives 1.2 g of 21-hydroxypregna-1,4,9(11)-trieno[16α,17-b][1,4]dioxane-3,20-dione, 21-acetate.

G. 9,11β-Dichloro-21-hydroxypregna-1,4-dieno[16α,17-b]-[1,4]dioxane-3,20-dione, 21-acetate A solution of 1.2 g of 21-hydroxypregna-1,4,9(11)-trieno[16α,17-b][1,4]dioxane-3,20-dione, 21-acetate and 5.0 g of lithium chloride in 50 ml of glacial acetic acid is stirred at 0°–5°C and 413 mg of N-chlorosuccinimide is added. A solution of 126 mg of dry hydrogen chloride in 2 ml of tetrahydrofuran is added and the resulting mixture is stirred at room temperature for 2 hours, poured into 600 ml of cold water, and extracted with chloroform. The chloroform solution is washed with water, dried and evaporated in vacuo to give 1.31 g of crude product. This material is plate chromatographed on three 20 × 20 cm – 2 mm silica gel plates. After two developments with 1:1 chloroform-ethyl acetate the UV-active band of intermediate $R_f$ is excised and eluted with ethyl acetate to give 735 mg of material. Recrystallization from methanol yields 540 mg of material, melting point 256°–258°C, dec. This is combined with 137 mg of material obtained by rechromatographing the mother liquors, and recrystallized from methanol to give 575 mg of 9,11β-dichloro-21-hydroxypregna-1,4-dieno[16α,17-b][1,4]dioxane-3,20-dione, 21-acetate.

Anal. Calc'd. for $C_{25}H_{30}Cl_2O_6$: C, 60.36; H, 6.08; Cl, 14.26 Found: C, 60.09; H, 5.83; Cl, 14.23.

EXAMPLE 2

9,11β-Dichloro-5'ε-ethoxy-21hydroxypregn-4-eno-[16α,17-b][1,4]dioxane-3,20-dione, 21-propionate A. 16α-(2,2-Diethoxyethoxy)-11β,17,21-trihydroxypregn-4-ene-3,20-dione A solution of 2,2-diethoxy-1-diazoethane (prepared from 0.0935 mole of N-2,2-diethoxyethyl urea by the method of W. Kirmse and B. Buschhoff, Chem. Ber., 100, 1491 (1967)) in 300 ml of 3:2 ether pentane is diluted with 100 ml of methanol and cooled to 0°C. 11β,16α,17,21-Tetrahydroxypregn-4-ene-3,20-dione, 16,17-cycloborate is added in portions until nitrogen evolution ceases. The solvent is removed in vacuo and the residue is recrystallized from methanol to yield the title compound.

B. 5'ε-Ethoxy-11β,21-dihydroxypregn-4-eno-[16α,17-b][1,4]dioxane-3,20-dione

A slurry of 100 mg of p-toluenesulfonic acid in 250 ml of benzene is refluxed with a Dean-Stark trap. The first 50 ml of benzene-water azeotrope is discarded and Linde type 4A molecular sieves are added to the trap. After 30 minutes at reflux, the solution is cooled and 2 mmoles of 16α-(2,2-diethoxyethoxy)-11β,17,21-trihydroxypregn-4-ene-3,20-dione is added. The resulting slurry is refluxed for 2 hours under nitrogen, cooled, diluted with chloroform, washed with 5% sodium bicarbonate solution, water, dried and evaporated to yield the title compound.

C. 5'ε-Ethoxy-11β,21-dihydroxypregn-4-eno[16α,17-b]-[1,4]dioxane-3,20-dione, 21-propionate A solution of 1.0 g of 5'ε-ethoxy-11β,21-dihydroxypregn-4-eno[16α,17-b][1,4]dioxane-3,20-dione in 20 ml of pyridine is stirred for 4 hours at room temperature with 2 ml of propionic anhydride. The solvent and excess anhydride are removed in vacuo, and the residue is dissolved in chloroform and washed with 5% hydrochloric acid, water, 5% sodium bicarbonate solution, dried and evaporated to give the title compound.

D. 5'ε-Ethoxy-21-hydroxypregna-4,9(11)-dieno[16α,17-b]-[1,4]dioxane-3,20-dione, 21-propionate A mixture of 5'ε-ethoxy-11β,21-dihydroxypregn-4-eno-[16α,17-b][1,4]dioxane-3,20-dione, 21-propionate (4 mmoles), 75 ml of dimethylformamide, 37.5 ml of pyridine, and 15 ml of methanesulfonyl chloride is stirred at 0°C for 75 minutes, poured into cold dilute hydrochloric acid, and the resulting mixture extracted with chloroform. The chloroform solution is dried and evaporated in vacuo to yield the title compound.

E. 9,11β-Dichloro-5'ε-ethoxy-21-hydroxypregn-4-eno-[16α,17-b][1,4]dioxane-3,20-dione, 21-propionate A solution of 5'ε-ethoxy-21-hydroxypregna-4,9(11)-dieno[16α,17-b][1,4]dioxane-3,20-dione, 21-propionate (1.4 mmoles) and 2.5 g of lithium chloride in 25 ml of glacial acetic acid is stirred at 0°–5°C and 207 mg of N-chlorosuccinimide is added. A solution of 63 mg of dry hydrogen chloride in 1 ml of tetrahydrofuran is added and the resulting mixture is stirred at room temperature for 2 hours, poured into 300 ml of cold water, and extracted with chloroform. The chloroform solution is washed with water, dried and evaporated in vacuo to yield the title compound.

EXAMPLE 3

9,11β,21-Trichloro-5'ε-ethoxy-pregn-4-eno[16α,17-b][1,4]dioxane-3,20-dione

A. 5'ε-Ethoxy-21-hydroxypregna-4,9(11)-dieno[16α,17-b]-[1,4]dioxane-3,20-dione, 21-mesylate A mixture of 5'ε-ethoxy-11β,21-dihydroxypregn-4-eno-[16α,17-b][1,4]dioxane-3,20-dione, (4 mmoles, prepared as described in Example 2B), 75 ml of dimethylformamide, 37.5 ml of pyridine, and 15 ml of methanesulfonyl chloride is stirred at 0°C for 75 minutes, poured into cold dilute hydrochloric acid, and the resulting mixture extracted with chloroform. The chloroform solution is dried and evaporated in vacuo to yield the title compound.

B. 9,11β-Dichloro-5'ε-ethoxypregn-4-eno[16α,17-b]-[1,4]dioxane-3,20-dione, 21-mesylate A solution of 5'ε-ethoxy-21-hydroxypregna-4,9(11)-dieno[16α,17-b][1,4]dioxane-3,20-dione, 21-mesylate (1.4 mmoles) and 2.5 g of lithium chloride in 25 ml of glacial acetic acid is stirred at 0°–5°C and 207 mg of N-chlorosuccinimide is added. A solution of 63 mg of dry hydrogen chloride in 1 ml of tetrahydrofuran is added and the resulting mixture is stirred at room tem- D. 21-Chloro-5'ε-hydroxypregna-1,4,9(11)-trieno-[16α,17-b][1,4]dioxane-3,20-dione, 5'ε-benzoate A mixture of 21-chloro-5'ε,11β-dihydroxypregna-1,4-dieno[16α,17-b][1,4]dioxane-3,20-dione, 5'ε-benzoate (2.8 mmoles), 52 ml of dimethylformamide 26 ml of pyridine and 11 ml of methanesulfonyl chloride is stirred at 0°C for 75 minutes, poured into cold dilute hydrochloric acid, and the resulting mixture extracted with chloroform. The chloroform solution is dried and evaporated in vacuo to yield the title compound.

E. 9,11β,21-Trichloro-5'ε-hydroxypregna-1,4-dieno-[16α,17-b][1,4]dioxane-3,20-dione, 5'ε-benzoate A solution of 21-chloro-5'ε-hydroxypregna-1,4,9(11)-trieno[16α,17-b][1,4]dioxane-3,20-dione, 5'ε-benzoate (2 mmoles) and 3.6 g of lithium chloride in 36 ml of glacial acetic acid is stirred at 0°–5°C and 296 mg of N-chlorosuccinimide is added. A solution of 90 mg of dry hydrogen chloride in 1.45 ml of tetrahydrofuran is added and the resulting mixture is stirred at room temperature for 2 hours, poured into 220 ml of cold water, and extracted with chloroform. The chloroform solution is washed with water, dried and evaporated in vacuo to yield the title compound.

EXAMPLE 7

9,11β-Dichloro-2',3'-dihydro-21-hydroxy-5'-phenylpregna-1,4-dieno[16α,17-b][1,4]dioxin-3,20-dione, 21-acetate A. 2-Phenyl-3-diazo-1-propene
 a. N-(2-Phenyl-2-propenyl)pthalimide A mixture of 60 g of potassium pthalimide and 66.4 g of α-bromoethyl styrene (prepared by the method of S. F. Reed, Jr., *J. Org. Chem.*, 30, 3258 (1965)) in 150 ml of dimethylformamide is refluxed for 2 hours, cooled, and diluted with 400 ml of water. The resulting solid is filtered and dried in vacuo to give 83.4 g of N-(2-phenyl-2-propenyl)-pthalimide. A small sample that is recrystallized from acetone-hexane has a melting point of 118°–121°C.

b. N-(2-Phenyl-2-propenyl)ethyl carbamate

A solution of 83 g of N-(2-phenyl-2-propenyl)pthalimide and 30 g of 99% hydrazine-hydrate is refluxed for 270 minutes and cooled. The slurry is treated with 125 ml of concentrated hydrochloric acid and filtered. The solid is washed with four 100 ml portions of water and the filtrate is evaporated in vacuo to a volume of 300 ml. This solution is cooled and mixed with a solution of 60 g of sodium hydroxide in 250 ml of cold water. The resulting solution is extracted with four 200 ml portions of ether and the ether solution is dried and evaporated in vacuo to give 30.7 g of oil. The oil is dissolved in 250 ml of ether, cooled to 0°C, and 33 g of ethyl chloroformate is added. A solution of 12 g of sodium hydroxide in 30 ml of water is added simultaneously with the second half of the ethyl chloroformate solution. After 1 hour at 10°C, the ether layer is washed with 5% hydrochloric acid, dried, and evaporated in vacuo to give 41.7 g of oil. Trituration with hexane and filtration gave 33 g of N-(2-phenyl-2-propenyl)ethyl carbamate, melting point 41°–42.5°C.

c. N-Nitroso-N-(2-phenyl-2-propenyl)ethyl carbamate

A solution of 21 ml (29.4 g) of nitrosyl chloride in 60 ml of pyridine (prepared at −25°C) is added over a period of 15 minutes to a solution of 57 g of N-(2-phenyl-2-propenyl)ethyl carbamate in 400 ml of pyridine at −5°C. The solution is stirred for 15 minutes and poured into 4 liters of cold water. The oil which separates is extracted into ether (three 600 ml portions) and the ether extract is washed successively with 1 liter of 10% hydrochloric acid, water, 1 liter of 5% sodium bicarbonate solution, and dried. Solvent removal gives 63 g of red oil that shows only minor impurities by TLC.

d. 2-Phenyl-3-diazo-1-propene

A solution of 63 g of N-nitroso-N-(2-phenyl-2-propenyl)ethyl carbamate in 300 ml of ether is added to 300 ml of 3M sodium methoxide in methanol at −1° to −2°C over a period of 30 minutes. The solution is stirred for a further hour and then poured into 2 liters of ice water and 100 ml each of ether and pentane. The organic layer is separated and kept at 0°C while the aqueous layer is extracted with 300 ml of ether. The combined organic layer is washed with two 1 liter portions of ice water, dried for 10 minutes at 0°C over NaOH pellets, and filtered to give 700 ml of red solution.

B.  11β,17,21-Trihydroxy-16α-(2-phenyl-2-propenyloxy)-pregna-1,4-diene-3,20-dione A solution of 1-diazo-2-phenyl-2-propene (prepared from 0.3 mole of N-nitrosourethane precursor) in methanolether at 0° is treated with 11β,16α,17,21-tetrahydroxypregna-1,4-diene-3,20-dione, 16,17-cycloborate (84 mmoles) until nitrogen evolution ceases. Solvent removal gives the title compound.

C.  11β,17,21-Trihydroxy-16α-(2-phenyl-2-propenyloxy)-pregna-1,4-diene-3,20-dione, 21-acetate Acetylation of 11β,17,21-trihydroxy-16α-(2-phenyl-2-propenyloxy)pregna-1,4-diene-3,20-dione (30 mmoles) is accomplished with 100 ml of pyridine and 5 ml of acetic anhydride. After 4 hours at room temperature the solvent is removed in vacuo and a chloroform solution of the residue washed with dilute hydrochloric acid, water, dilute sodium bicarbonate solution and dried. Solvent removal gives the title compound.

D.  11β,17,21-Trihydroxy-16α-[(2-phenyloxiranyl)-methoxy]-pregna-1,4-diene-3,20-dione, 21-acetate A solution of 11β,17,21-trihydroxy-16α-(2-phenyl-2-propenyloxy)pregna-1,4-diene-3,20-dione, 21-acetate (8 mmoles) in 100 ml of dichloromethane is stirred with 1.6 g of m-chloroperbenzoic acid. After 3 hours the solution is washed with a mixture of dilute sodium bicarbonate solution and dilute sodium sulfite solution, dried, and evaporated to give the title compound.

E.  11β,17,21-Trihydroxy-16α-(2-oxo-2-phenylethoxy)-pregna-1,4-diene-3,20-dione, 21-acetate A solution of 11β,17,21-trihydroxy-16α-[(2-phenyloxiranyl)methoxy]-pregna-1,4-diene-3,20-dione, 21-acetate (6 mmoles) in 60 ml of tetrahydrofuran is stirred with a solution of 2 g of periodic acid in 10 ml of water for 3 hours. The solution is diluted with water and extracted with chloroform. The chloroform solution is washed with dilute sodium bicarbonate solution, dried, and evaporated to give the title compound.

F.  17,21-Dihydroxy-16α-(2-oxo-2-phenylethoxy)-pregna-1,4,9(11)-triene-3,20-dione, 21-acetate A solution of 11β,17,21-trihydroxy-16α-(2-oxo-2-phenylethoxy)-pregna-1,4-diene-3,20-dione, 21-acetate (4 mmoles) in 40 ml of dimethylformamide and 20 ml of pyridine is stirred with 10 ml of methanesulfonyl chloride for 60 minutes at 0°C, poured into dilute hydrochloric acid and extracted with chloroform. The chloroform solution is washed with water, dried, and evaporated to give the title compound.

G. 9,11β-Dichloro-17,21-dihydroxy-16α-(2-oxo-2-phenylethoxy)-pregna-1,4-diene-3,20-dione, 21-acetate A solution of 17,21-dihydroxy-16α-(2-oxo-2-phenylethoxy)pregna-1,4,9(11)-triene-3,20-dione, 21-acetate (1.4 mmoles) and 2.52 g of lithium chloride in 25 ml of glacial acetic acid is stirred at 0°–5°C and 209 mg of N-chlorosuccinimide is added. A solution of 63 mg of dry hydrogen chloride in 1 ml of tetrahydrofuran is added and the resulting mixture stirred at room temperature for 2 hours, poured into 130 ml of cold water, and extracted with chloroform. The chloroform solution is washed with water, dried, and evaporated to give the title compound.

H. 9,11β-Dichloro-2',3'-dihydro-21-hydroxy-5'-phenylpregna-1,4-dieno[16α,17-b][1,4]dioxin-3,20-dione, 21-acetate A slurry of 100 mg of p-toluenesulfonic acid in 100 ml of benzene is refluxed for 1 hour with a Dean-Stark trap filled with molecular sieve. The solution is cooled and 9,11β-dichloro-21-hydroxy-16α-(2-oxo-2-phenylethoxy)pregna-1,4-diene-3,20-dione, 21-acetate (1 mmole) is added. After refluxing for 30 minutes under nitrogen the solution is cooled, washed with 5% sodium bicarbonate solution, dried, and evaporated in vacuo to give the title compound.

EXAMPLE 8

9,11β,21-Trichloro-2',3'-dihydro-5'-methylpregna-1,4-dieno[16α,17-b][1,4]dioxane-3,20-dione A. 21-Chloro-11β,16α,17-trihydroxypregna-1,4-diene-3,20-dione, 16,17-cycloborate A solution of 21-chloro-11β,16α,17-trihydroxypregna-1,4-diene-3,20-dione (20 mmoles) and boric anhydride (20 g) in 300 ml of methanol is refluxed for 1 hour, cooled, diluted with water, and filtered to give the title compound B. 21-Chloro-11β,17-dihydroxy-16α-(2-methyl-2-propenyloxy)pregna-1,4-dieno-3,20-dione A solution of 2-methyl-1-diazo-2-propene (prepared from 0.3 mole of precursor) in methanol-ether at 0°C is treated with 21-chloro-11β,16α,17-trihydroxypregna-1,4-diene-3,20-dione, 16,17-cycloborate until nitrogen evolution ceases. Solvent removal gives the title compound.

C. 21-Chloro-11β,17-dihydroxy-16α-[(2-methyloxiranyl)-methoxy]pregna-1,4-diene-3,20-dione A solution of 21-chloro-11β,17-dihydroxy-16α-(2-methyl-2-propenyloxy)pregna-1.4-diene-3,20-dione (16 mmoles) in 300 ml of dichloromethane is stirred with 3.2 g of m-chloroperbenzoic acid for 3 hours. The solution is washed with a mixture of 5% sodium bicarbonate solution and 5% sodium sulfite solution, dried, and evaporated to give the title compound.

D. 21-Chloro-11β,17-dihydroxy-16α-(2-oxopropoxy)pregna-1,4-diene-3,20-dione

A solution of 21-chloro-11β,17-dihydroxy-16α-[(2-methyloxiranyl)methoxy]pregna-1,4-diene-3,20-dione (12 mmoles) in 200 ml of tetrahydrofuran is stirred with a solution of 10 g of periodic acid in 20 ml of water for 3 hours. The slurry is diluted with water and extracted with chloroform. The chloroform solution is dried and evaporated in vacuo to give the title compound.

E. 21-Chloro-17-hydroxy-16α-(2-oxopropoxy)-pregna-1,4,9(11)-triene-3,20-dione

A solution of 21-chloro-11β,17-dihydroxy-16α-(2-oxopropoxy)pregna-1,4-diene-3,20-dione (10 mmoles) in 40 ml of dimethylformamide and 20 ml of pyridine is stirred at 0°C for 75 minutes with 10 ml of methanesulfonyl chloride. The mixture is poured into cold, dilute hydrochloric acid and extracted with chloroform. The chloroform solution is dried and evaporated to give the title compound.

F. 9,11β,21-Trichloro-17-hydroxy-16α-(2-oxopropoxy)pregna-1,4-diene-3,20-dione

A solution of 21-chloro-17-hydroxy-16α-(2-oxopropoxy)pregna-1,4,9(11)-triene-3,20-dione (4 mmoles) and 7.2 g of lithium chloride in 72 ml of glacial acetic acid is stirred at 0°–5°C and 592 mg of N-chlorosuccinimide is added. A solution of 180 mg of dry hydrogen chloride in 2.9 ml of tetrahydrofuran is added and the resulting mixture stirred at room temperature for 2 hours, poured into 400 ml of cold water, and extracted with chloroform. The chloroform solution is washed with water, dried, and evaporated to give the title compound.

G. 9,11β,21-Trichloro-2',3'-dihydro-5'-methylpregna-1,4-dieno[16α,17-b][1,4]dioxin-3,20-dione A slurry of 200 mg of p-toluenesulfonic acid in 200 ml of benzene is refluxed for 1 hour with a Dean-Stark trap filled with molecular sieve. The resulting solution is cooled and 9,11β,21-trichloro-17-hydroxy-16α-(2-oxopropoxy)-pregna-1,4-diene-3,20-dione (3 mmoles) is added. After refluxing for 2 hours the solution is cooled, washed with dilute sodium bicarbonate solution and dried. Solvent removal yields the title compound.

EXAMPLE 9

9-Chloro-11β-fluoro-5'ε,21-dihydroxypregn-4-eno[16α,17-b][1,4]dioxane-3,20-dione, 21-acetate A. 16α-Allyloxy-11β,17,21-trihydroxypregn-4-ene-3,20-dione 11β,16α,17,21-Tetrahydroxypregn-4-ene-3,20-dione, 16,17-cycloborate is added to a solution of vinyl diazomethane in 1:1 methanol-ether at 0°C until nitrogen evolution ceases. The solvent is evaporated to yield the title compound.

B. 16α-Allyloxy-11β,17,21-trihydroxypregn-4-ene-3,20-dione, 21-acetate

A solution of 16α-allyloxy-11β,17,21-trihydroxypregn-4-ene-3,20-dione (22 mmoles) in 100 ml of pyridine is stirred for 2 hours with 10 ml of acetic anhydride and the solvent is then removed in vacuo. A solution of the residue in chloroform is washed with 5% hydrochloric acid, water, 10% sodium bicarbonate solution, water, and dried. Solvent removal in vacuo yields the title compound.

C. 16α-(Allyloxy)-17,21-dihydroxypregna-4,9(11)-diene-3,20-dione, 21-acetate

A solution of 16α-(allyloxy)-11β,17,21-trihydroxypregn-4-ene-3,20-dione (10 mmoles) in 100 ml of dimethylformamide and 50 ml of pyridine is stirred for 90 minutes at 0°C with 20 ml of methanesulfonyl chloride. The solution is poured into excess 5% hydrochloric acid and extracted with chloroform. The chloroform solution is dried and evaporated to give the title compound.

D. 16α-(Allyloxy)-9-chloro-11β-fluoro-17,21-dihydroxypregn-4-ene-3,20-dione, 21-acetate A solution of 16α-(allyloxy)-17,21-dihyroxypregna-4,9(11)-diene-3,20-dione, 21-acetate (0.5 mmoles)

and N-chlorosuccinimide (67 mg, 0.5 mmoles) in dichloromethane is added to a mixture of anhydrous hydrogen fluoride (3.42 g) and anhydrous tetrahydrofuran (6 g) in a polyethylene bottle at −80°C. After 1 hour, the mixture is stirred for 30 minutes at −20°C and then added slowly to cold sodium carbonate solution. Extraction with chloroform, drying of the extract, and solvent removal gives the title compound.

E. 9-Chloro-11β-fluoro-17,21-dihydroxy-16α-(oxiranylmethoxy)pregn-4-ene-3,20-dione, 21-acetate A solution of 16α-(allyloxy)-9-chloro-11β-fluoro17,21-dihydroxypregn-4-ene-3,20-dione, 21-acetate (1.4 mmoles) in 20 ml of dichloromethane is stirred with 300 mg of m-chloroperbenzoic acid for 72 hours. The solution is washed with a cold mixture of dilute sodium bicarbonate and dilute sodium sulfite solution and dried. Solvent removal gives the title compound.

F. 9-Chloro-11β-fluoro-5′ε,21-dihydroxypregn-4-eno[16α,17-b][1.4]dioxane-3,20-dione, 21-acetate A solution of 9-chloro-11β-fluoro-17,21-dihydroxy-16α-(oxiranylmethoxy)pregn-4-ene-3,20-dione, 21-acetate (1 mmole) in 20 ml of tetrahydrofuran is stirred with 1 g of periodic acid in 4 ml of water for 7 hours. The solution is diluted with water and extracted with chloroform. Drying of this solution and solvent removal gives the title compound.

EXAMPLE 10

9,21-Dichloro-11β-fluoro-5′ε-hydroxypregna-4-eno-[16α,17-b][1,4]-dioxane-3,20-dione, 5′-butyrate A. 16α-Allyloxy-11β,17,21-trihydroxypregn-4-ene-3,20-dione, 21-methanesulfonate A solution of 16α-allyloxy-11β, 17,21-trihydroxypregn-4-ene-3,20-dione (5 mmoles, prepared as described in Example 9A) in 50 ml of pyridine is stirred at 0°C under nitrogen for 150 minutes with 1 ml of methanesulfonyl chloride. The resulting solution is poured into cooled 5% hydrochloric acid and extracted with chloroform. The chloroform solution is washed with water, dried, and evaporated in vacuo to yield the title compound.

B. 16α-Allyloxy-21-chloro-11β,17-dihydroxypregn-4-ene-3,20-dione

A solution of 16α-allyloxy-11β,17,21-trihydroxypregn-4-ene-3,20-dione, 21-methanesulfonate (4.6 mmoles) in 60 ml of dimethylformamide is refluxed for 1 hour under nitrogen with 5 g of lithium chloride. The solution is cooled, diluted with water and filtered. The solid is dissolved in chloroform, washed with 5% hydrochloric acid, water, dried, and evaporated in vacuo to yield the title compound.

C. 21-Chloro-11β,17-dihydroxy-16α-(oxiranylmethoxy)-pregn-4-ene-3,20-dione

A solution of 16α-allyloxy-21-chloro-11β,17-dihydroxypregn-4-ene-3,20-dione (3.8 mmoles) in 50 ml of dichloromethane is stirred with 0.76 g of m-chloroperbenzoic acid for 19 hours at room temperature. The resulting solution is washed with a mixture of 10% potassium carbonate solution and 10% sodium sulfite solution, dried, and evaporated in vacuo to yield the title compound.

D. 21-Chloro-5′ε,11β-dihydroxypregn-4-eno-[16α,17-b][1,4]dioxane-3,20-dione

A solution of 21-chloro-11β,17-dihydroxy-16α-(oxiranylmethoxy)pregn-4-ene-3,20-dione (3 mmoles) in 20 ml of tetrahydrofuran is stirred with a solution of 2 g of periodic acid in 7 ml of water for 6¾ hours. The solution is diluted with water and extracted with chloroform. The chloroform extract is washed with 5% sodium bicarbonate solution, dried and evaporated in vacuo to yield the title compound.

E. 21-Chloro-5′ε,11β-dihydroxypregn-4-eno[16α,17-b][1,4]dioxane-3,20-dione, 5′-butyrate A solution of 21-chloro-5′ε,11β-dihydroxypregn-4-eno[16α,17-b][1,4]dioxane-3,20-dione (5.5 mmoles) in 30 ml of pyridine is stirred at room temperature with 6 mmoles of n-butyryl chloride for 4 hours. The mixture is diluted with chloroform, washed with 5% hydrochloric acid, water, 5% sodium bicarbonate solution, and dried. Solvent removal gives the title compound.

F. 21-Chloro-5′ε-hydroxypregna-4,9(11)-dieno-[16α,17-b][1,4]dioxane-3,20-dione, 5′-butyrate A mixture of 21-chloro-5′ε,11β-dihydroxypregn-4-eno-[16α,17-b][1,4]dioxane-3,20-dione, 5′-butyrate (4 mmoles), 75 ml of dimethylformamide, 37.5 ml of pyridine and 12 ml of methanesulfonyl chloride is stirred at 0°C for 75 minutes, poured into cold dilute hydrochloric acid, and the resulting mixture extracted with chloroform. The chloroform solution is dried and evaporated in vacuo to yield the title compound.

G. 9,21-Dichloro-11β-fluoro-5′ε-hydroxypregn-4-eno-[16α,17-b][1,4]dioxaane-3,20-dione, 5′-butyrate A mixture of 21-chloro-5′ε-hydroxypregna-4,9(11)-dieno[16α,17-b][1,4]dioxane-3,20-dione, 5′-butyrate (2 mmoles) and N-chlorosuccinimide (260 mg, 2 mmoles) in dry dichloromethane is added to a mixture of 10.13 g of anhydrous hydrogen fluoride and 18 g of anhydrous tetrahydrofuran in a polyethylene bottle at −80°C. After 1 hours the mixture is stirred an additional 2 hours at 0°C and poured cautiously into cold sodium carbonate solution. Extraction with chloroform gives the title compound.

EXAMPLE 11

9,21-Dichloro-11β-fluoropregna-1,4-dieno-[16α,17-b][1,4]dioxane-3,20-dione

A. 21-Chloro-11β,17-dihydroxy-16α-[2-(tetrahydropyran-2-yloxy)ethoxy]-pregna-1,4-diene-3,20-dione A solution of 2-(tetrahydropyran-2-yloxy)-1-diazoethane (prepared from 0.21 mole of N-[2-(tetrahydropyran-2-yloxy)ethyl]urea as described in Example 1) in 400 ml of 3:1 ether-pentane is diluted with 100 ml each of ether and methanol at 0°C and stirred vigorously while 21-chloro-11β,16α,17-trihydroxypregna-1,4-diene-3,20-dione, 16,17-cycloborate (12 mmoles) is added. After nitrogen evolution ceases the solvents are removed in vacuo to yield the title compound.

B. 21-Chloro-11β,17-dihydroxy-16α-(2-hydroxyethoxy)-pregna-1,4-diene-3,20-dione

A solution of 21-chloro-11β,17-dihydroxy-16α-[2-(tetrahydropyran-2-yloxy)ethoxy]pregna-1,4-diene-3,20-dione (8.4 mmoles) in 50 ml of acetic acid and 50 ml of water is stirred at room temperature for 6 hours, diluted with cold water, and the resulting solid filtered and dried in vacuo to yield the title compound.

C. 21-Chloro-11β,17-dihydroxy-16α-(2-mesyloxyethoxy)pregna-1,4-diene-3,20-dione

A solution of 21-chloro-11β,17-dihydroxy-16α-(2-hydroxyethoxy)pregna-1,4-diene-3,20-dione (7.6 mmoles) in 30 ml of pyridine is cooled to 0°C and 1 ml of methanesulfonyl chloride is added. After 2 hours the mixture is poured into cold dilute hydrochloric acid and extracted with chloroform. The chloroform solution is dried and evaporated in vacuo to yield the title compound.

D. 21-Chloro-11β-hydroxypregna-1,4-dieno-[16α,17-b][1,4]dioxane-3,20-dione

A solution of 21-chloro-11β,17-dihydroxy-16α-(2-mesyloxyethoxy)pregna-1,4-diene-3,20-dione (6 mmoles) in 100 ml of dimethylsulfoxide is stirred at 110°C under nitrogen with 3 g of sodium bicarbonate (dried at 110°C in vacuo). After 1 hour the slurry is cooled, poured into 2 liters of 2.5% hydrochloric acid, and extracted with chloroform. The chloroform solution is washed with dilute hydrochloric acid, dried, evaporated in vacuo to yield the title compound.

E. 21-Chloropregna-1,4,9(11)trieno[16α,17-b][1,4]dioxane-3,20-dione

A mixture of 21-chloro-11β-hydroxypregna-1,4-dieno-[16α,17-b][1,4]dioxane-3,20-dione (4 mmoles), 40 ml of dimethylformamide, 20 ml of pyridine, and 10 ml of methanesulfonyl chloride is stirred at 0°C for 75 minutes, poured into cold dilute hydrochloric acid, and the resulting mixture extracted with chloroform. The chloroform solution is dried and evaporated in vacuo to yield the title compound.

F. 9,21-Dichloro-11β-fluoropregna-1,4-dieno-]16α,17-b][1,4]dioxane-3,20-dione

A mixture of 21-chloropregna-1,4,9(11)-trieno-[16α,17-b][1,4]dioxane-3,20-dione (1.9 mmoles) and N-chlorosuccinimide (247 mg, 1.9 mmoles) in dry methylene chloride is added slowly to a mixture of 10.2 g of anhydrous hydrogen fluoride and 18 g of tetrahydrofuran at −80°C. After 1 hour the mixtrue is stirred a further hour at 0°C and poured into cold sodium bicarbonate solution. The title compound is obtained by extraction with chloroform, drying, and solvent removal in vacuo.

EXAMPLE 12

9-Chloro-11β-fluoro-2',3'-dihydro-21-hydroxypregn-4-eno[16α,17-b]][1,4]dioxin-3,20-dione, 21-acetate A solution of 9-chloro-11β-fluoro-5'ϵ,21-dihydroxypregn-4-eno[16α,17-b][1,4]dioxane-3,20-dione, 21-acetate (0.6 mmole prepared as described in Example 9) is added to an anhydrous solution of 70 mg of p-toluenesulfonic acid in 60 mg of benzene. After refluxing for 6 hours, the solution is cooled, washed with dilute sodium bicarbonate solution, dried, and evaporated to give the title compound.

EXAMPLE 13

9-Chloro-11ϵ-fluoro-21-hydroxypregn-4-eno-[16α,17-b][1,4]dioxane-3,5,20-trione, 21-acetate A solution of 9-chloro-11β-fluoro-5'ϵ,21-dihydroxypregn-4-eno[16α,17-b][1,4]dioxane-3,20-dione, 21-acetate (1 mmole, prepared as described in Example 9) in 100 ml toluene is refluxed in a Dean Stark apparatus with 7 g of Fetizon's reagent under nitrogen for 14 hours, cooled and filtered. The filtrate is evaporated to give the title compound.

EXAMPLE 14

9,11β-Dichloro-21-hydroxypregna-1,4-dieno-[16α,17-b][1,4]dioxane-3,20-dione

A solution of 9,11β-dichloro-21-hydroxypregna-1,4-dieno[16α,17-b][1,4]dioxane-3,20-dione, 21-acetate (2 mmoles, prepared as described in Example 1) in 40 ml of methanol is stirred at 0°C with 4 ml of 10% potassium carbonate solution. The resulting solution is acidified with 1 ml of glacial acetic acid and diluted with water to give the title compound.

EXAMPLE 15

9,11β-Dichloro-21-hydroxypregna-1,4-dieno[16α,17-b]-[1,4]dioxane-3,20-dione, 21-cyclohexanecarboxylate A solution of 9,11β-dichloro-21-hydroxypregna-1,4-dieno[16α,17-b][1,4]dioxane-3,20-dione (1.6 mmoles, prepared as described in Example 14) in 20 ml of pyridine is stirred with 400 mg of cyclohexanecarbonyl chloride for 2 hours. The solution is diluted with chloroform, washed with 5% hydrochloric acid, dried, and evaporated to give the title compound.

EXAMPLE 16

9,11β-Dichloro-5'ϵ-ethoxypregn-4-eno[16α,17-b]-[1,4]dioxane-3,20-dione

A. 5'-Ethoxypregna-4,9(11)dieno[16α,17-b][1,4]-dioxane-3,20-dione

A solution of 5'ϵ-ethoxy-21-hydroxypregna-4,9(11)-dieno[16α,17-b][1,4]dioxane-3,20-dione, 21-mesylate (4 mmoles, prepared as described in Example 3A) in 30 ml of dimethylformamide is refluxed for 2 hours with 2 g of lithium iodide. The solution is diluted with chloroform, washed with dilute hydrochloric acid, water, sodium bisulfite solution, dried, and evaporated to give the title compound.

B. 9,11β-Dichloro-5'ϵ-ethoxypregn-4-eno[16α,17-b]-[1,4]dioxane-3,20-dione

A solution of 5'ϵ-ethoxypregna-4,9(11)dieno[1-6α,17-b]-[1,4]dioxane-3,20-dione (1.4 mmoles) and 2.5 g of lithium chloride in 25 ml of glacial acetic acid is stirred at 0°–5°C and 207 ml of N-chlorosuccinimide is added. A solution of 63 mg of dry hydrogen chloride in 1 ml of tetrahydrofuran is added and the resulting mixture is stirred at room temperature for 2 hours, poured into 300 ml of cold water, and extracted with chloroform. The chloroform solution is washed with water, dried and evaporated in vacuo to yield the title compound.

EXAMPLE 17

9,11β-Dichloro-5'ϵ,21-dihydroxypregn-4-eno-[16α,17-b][1,4]dioxane-3,20-dione

A solution of 9,11β-dichloro-5'ϵ,21-dihydroxypregn-4-eno[16α,17-b][1,4]dioxane-3,20-dione, 5',21-diacetate (.1 mmole, prepared as described in Example 4) in 40 ml of methanol at 0°C is treated with 4 ml of 10 % potassium carbonate solution. After 2 hours the solution is acidified with 2 ml of acetic acid, diluted with water, and extracted with chloroform to give the title compound.

EXAMPLE 18

9,11β-Dichloro-5'ϵ,21-dihydroxy-6α-methylpregna-1,4-dieno[16α, 17-b][1,4]dioxane-3,20-dione, 5'ϵ,21-diacetate A. 11β,16α,17,21-Tetrahydroxy-6α-methylpregna-1,4-diene-3,20-dione, 16,17-cycloborate A solution of 8 g of 11β,16α,17,21-tetrahydroxy-6α-methylpregna-1,4-diene-3,20-dione in 200 ml of methanol is refluxed with 48 g of boric anhydride for 1 hour, cooled, diluted with water and filtered to give the title compound.

25

B. 16α-[(2,2-Diethoxy)ethoxy]-11β,17,21-trihydroxy-6α-methylpregna-1,4-diene-3,20-dione A solution of 2,2-diethoxy-1-diazoethane (prepared from 0.18 mole of precursor as described in Example 2A) in methanolether at 0°C is treated with 11β,16α,17,21-tetrahydroxy-6α-methylpregna-1,4-diene-3,20-dione, 16,17-cycloborate until nitrogen evolution ceases. The solution is evaporated to give the title compound.

5′ε,11β,21-Trihydroxy-6α-methylpregna-1,4-dieno[16α,17-b[]1,4]dioxane-3,20-dione A solution of 16α-[(2,2-diethoxy)ethoxy]-11β,17,21-trihydroxy-6α-methylpregna-1,4-diene-3,20-dione (10 mmoles) in 150 ml of tetrahydrofuran is refluxed for 3 hours with 15 ml of 2N hydrochloric acid. The solution is cooled, diluted with water, and extracted with chloroform. The chloroform solution is dried and evaporated to give the title compound.

D. 9,11β-Dichloro-5′ε,21-dihydroxy-6α-methylpregna-1,4-dieno[16α,17-b][1,4]dioxane-3,20-dione, 5′ε,21-diacetate Substituting 5′ε,11β,21-trihydroxy-6α-methylpregna-1,4-dieno[16α,17-b][1,4]dioxane-3,20-dione for the steroid reactant of Example 4B and proceeding as described in Example 4C and 4D the title compound is obtained.

EXAMPLE 19

9,11β,21-Trichloro-2′,3′-dihydro-5′-phenylpregna-1,4-dieno[16α,17-b][1,4]dioxin-3,20-dione A. 9,11β-Dichloro-17,21-dihydroxy-16α-(2-oxo-2-phenylethoxy)pregna-1,4-diene-3,20-dione A solution of 9,11β-dichloro-17,21-dihydroxy-16α-(2-oxo-2-phenylethoxy)pregna-1,4-diene-3,20-dione, 21-acetate (2 mmole, prepared as described in Example 7G) in 40 ml of methanol is stirred with 4 ml of 10% potassium carbonate solution at 0°C for 30 minutes, acidified with 2 ml of acetic acid, diluted with water, and extracted with chloroform to give the title compound.

B. 9,11β-Dichloro-17,21-dihydroxy-16α-(2-oxo-2-phenylethoxy)pregna-1,4-diene-3,20-dione, 21-methanesulfonate A solution of 9,11β-dichloro-17,21-dihydroxy-16α-(2-oxo-2-phenylethoxy)pregna-1,4-diene-3,20-dione (1.4 mmoles) in 20 ml of pyridine is stirred at 0°C with methanesulfonyl chloride (2 mmoles) for 2 hours. The solution is diluted with chloroform, washed with 5% hydrochloric acid, dried, and evaporated to give the title compound.

C. 9,11β,21-Trichloro-17-hydroxy-16α-(2-oxo-2-phenylethoxy)pregna-1,4-diene-3,20-dione A solution of 9,11β-dichloro-17,21-dihydroxy-16α-(2-oxo-2-phenylethoxy)pregna-1,4-diene-3,20-dione, 21-methanesulfonate (1 mmole) in 20 ml of dimethylformamide is heated at 80°C for 3 hours with 1 g of lithium chloride, cooled, diluted with water and filtered to give the title compound.

D. 9,11β,21-Trichloro-2′,3′-dihydro-5′-phenylpregna-1,4-dieno[16α,17-b][1,4]dioxin-3,20-dione A slurry of 100 mg of p-toluenesulfonic acid in 100 ml of benzene is refluxed for 1 hour with a Dean-Stark trap filled with molecular sieve. The solution is cooled and 9,11β,21-trichloro-17-hydroxy-16α-(2-oxo-2-phenylethoxy)pregna-1,4-diene-3,20-dione (1 mmole) is added. After refluxing for 30 minutes under nitrogen the solution is cooled, washed with 5% sodium bicarbonate solution, dried, and evaporated in vacuo to give the title compound.

What is claimed is:

1. A steroid having the structure

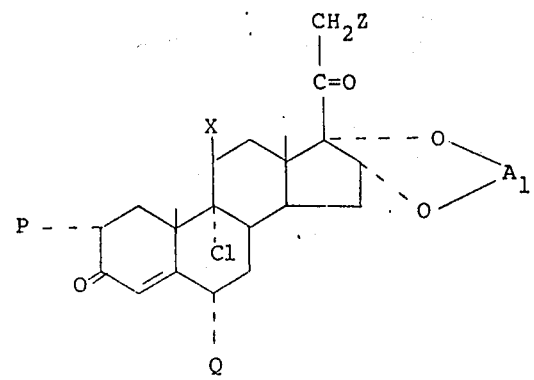

and the 1,2-dehydro and 6,7-dehydro derivatives thereof, wherein Z is hydrogen, hydroxy,

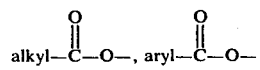

or halogen; X is chlorine or fluorine; $A_1$ is —$CH_2$—$CH_2$—,

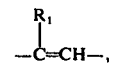

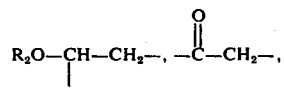

or

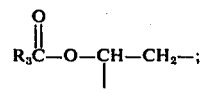

$R_1$ is hydrogen, alkyl or aryl; $R_2$ is hydrogen or alkyl; $R_3$ is alkyl, cycloalkyl or aryl; and P and Q are independent of each other and are hydrogen, methyl or halogen.

2. A steroid in accordance with claim 1 wherein $A_1$ is —$CH_2$—$CH_2$—.

3. A steroid in accordance with claim 1 wherein $A_1$ is

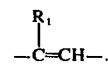

4. A steroid in accordance with claim 1 wherein $A_1$ is

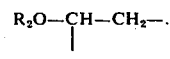

5. A steroid in accordance with claim 1 wherein $A_1$ is

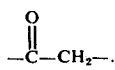

6. A steroid in accordance with claim 1 wherein $A_1$ is

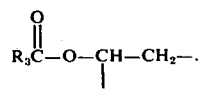

7. A steroid in accordance with claim 1 wherein X is chlorine.

8. A steroid in accordance with claim 1 wherein X is fluorine.

9. A steroid in accordance with claim 1 wherein P and Q are each hydrogen.

10. The steroid in accordance with claim 1 having the name 9,11β-dichloro-21-hydroxypregna-1,4-dieno[1-6α,17-b][1,4]dioxane-3,20-dione, 21-acetate.

* * * * *

UNITED STATES PATENT AND TRADEMARK OFFICE
CERTIFICATE OF CORRECTION

PATENT NO. : 3,971,773
DATED : July 27, 1976
INVENTOR(S) : Christopher M. Cimarusti et al.

It is certified that error appears in the above-identified patent and that said Letters Patent are hereby corrected as shown below:

Column 1, line 56, omit "or" before the formula.

Column 5, line 30, the formula should read

Column 10, line 31, "XVIII" should read --XVII--.
Column 11, line 67, "20°C" should read --0°C--.
Column 22, line 26, "dioxaane" should read --dioxane--.
Column 25, line 10, please add "C." before the title.

Signed and Sealed this

Fifteenth Day of February 1977

[SEAL]

Attest:

RUTH C. MASON
Attesting Officer

C. MARSHALL DANN
Commissioner of Patents and Trademarks